United States Patent
Kaneko

(10) Patent No.: US 8,968,648 B2
(45) Date of Patent: Mar. 3, 2015

(54) METHOD FOR RADIATION STERILIZATION OF HYDROPHILIC POLYMER-COATED MEDICAL DEVICE

(75) Inventor: Takashi Kaneko, Sagamihara (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 1057 days.

(21) Appl. No.: 12/990,993

(22) PCT Filed: Apr. 30, 2009

(86) PCT No.: PCT/JP2009/058456
§ 371 (c)(1),
(2), (4) Date: Nov. 4, 2010

(87) PCT Pub. No.: WO2009/139304
PCT Pub. Date: Nov. 19, 2009

(65) Prior Publication Data
US 2011/0058982 A1 Mar. 10, 2011

(30) Foreign Application Priority Data
May 16, 2008 (JP) ................. 2008-129854

(51) Int. Cl.
- A61L 2/08 (2006.01)
- A61M 25/00 (2006.01)
- A61M 25/09 (2006.01)

(52) U.S. Cl.
CPC . *A61L 2/08* (2013.01); *A61L 2/087* (2013.01); *A61M 25/002* (2013.01);
(Continued)

(58) Field of Classification Search
CPC ........................................................ A61L 2/08
USPC .......................................................... 422/22
See application file for complete search history.

(56) References Cited

U.S. PATENT DOCUMENTS 4,248,236 A * 2/1981 Linder ..................... 604/100.01
4,813,210 A 3/1989 Masuda et al.
(Continued)

FOREIGN PATENT DOCUMENTS

EP 1 252 898 A2 10/2002
EP 1 834 655 A1 9/2007
(Continued)

OTHER PUBLICATIONS

Office Action (Text of the Second Office Action) issued by the Chinese Patent Office on Apr. 27, 2013, in the corresponding Chinese Patent Application No. 200980113365.2, and an English Translation of the Office Action. (6 pages).
(Continued)

*Primary Examiner* — Sean E Conley
(74) *Attorney, Agent, or Firm* — Buchanan Ingersoll & Rooney PC

(57) ABSTRACT

A radiation sterilization method of a disposable medical device and a manufacturing method are provided, which method comprising the steps of packaging a disposable medical device, which has applied thereto with hydrophilic polymer coating, with a gas permeable packaging material, controlling a product moisture content of the thus packaged medical device by maintaining the device in a given humidity atmosphere for not less than a time at which an equilibrated moisture content is reached, and subjecting, to radiation sterilization, the medical device whose product moisture content has been controlled, so that an eluted matter is reduced in amount and a sliding performance is ensured according to the radiation sterilization method of the hydrophilic polymer-coated, disposable medical device and the manufacturing method.

12 Claims, 11 Drawing Sheets

(52) U.S. Cl.
CPC ........ *A61L 2202/24* (2013.01); *A61M 25/0017* (2013.01); *A61M 25/0045* (2013.01); *A61M 25/09* (2013.01); *A61M 2025/0046* (2013.01)
USPC .......................................................... 422/22

(56) References Cited

U.S. PATENT DOCUMENTS

| | | |
|---|---|---|
| 2002/0037943 A1 | 3/2002 | Madsen |
| 2005/0214443 A1 | 9/2005 | Madsen |
| 2006/0263404 A1 | 11/2006 | Nielsen et al. |
| 2008/0292496 A1 | 11/2008 | Madsen |

FOREIGN PATENT DOCUMENTS

| | | |
|---|---|---|
| JP | 52-099697 A | 8/1977 |
| JP | 61-073663 A | 4/1986 |
| JP | 62-074364 A | 4/1987 |
| JP | 4-285561 A | 10/1992 |
| JP | 06-285162 A | 10/1994 |
| JP | 2000-288085 A | 10/2000 |
| JP | 2002-530158 A | 9/2002 |
| JP | 2004-215709 A | 8/2004 |
| JP | 2005-095270 A | 4/2005 |
| JP | 2005-095271 A | 4/2005 |
| JP | 2005-334319 A | 12/2005 |
| JP | 2006-519039 A | 8/2006 |
| WO | WO 00 30696 A1 | 6/2000 |
| WO | WO 00/30696 A1 | 6/2000 |
| WO | WO 2004/075944 A2 | 9/2004 |
| WO | WO 2005/014055 A2 | 2/2005 |
| WO | WO 2006/117372 A1 | 11/2006 |
| WO | WO 2007/137699 A1 | 12/2007 |

OTHER PUBLICATIONS

International Search Report (PCT/ISA/210) issued on Jun. 9, 2009, by Japanese Patent Office as the International Searching Authority for International Application No. PCTJP2009/058456.
Extended European Search Report dated Jul. 28, 2011, issued in the corresponding European Patent Application No. 09746511.6-2113/2277554 (6 pages).
Office Action (Notification of the First Office Action) dated Nov. 30, 2012, issued in corresponding Chinese Patent Application No. 200980113365.2, and an English Translation of Office Action. (8 pages).
Office Action dated May 20, 2014, issued by the European Patent Office, in the corresponding European Patent Application No. 09 746 511.6. (5 pages).

* cited by examiner

METHOD FOR RADIATION STERILIZATION OF HYDROPHILIC POLYMER-COATED MEDICAL DEVICE

TECHNICAL FIELD

This invention relates to a method for radiation sterilization of medical devices adapted for treatment and diagnosis by insertion into a living body. More particularly, the invention relates to a method for radiation sterilization of disposable medical devices applied with a hydrophilic coating used to administer treatment and diagnosis by insertion thereof into the human body from digestive organs, digestive glands, uritary organs, genitals, blood vessels (artery, vein), lymph channels, ear and nose, or skin and also, to a manufacturing method.

BACKGROUND ART

Disposable medical devices have been widely accepted from the standpoint of the prevention of hospital infection and medical economy, and many improvements have been added thereto. For instance, there have been in practical use those devices, used by insertion in to a living body, having a hydrophilic coating, which is provided on the surface of a medical device, is swollen with a body fluid or a physiological saline solution and shows lubricity. The role of the hydrophilic coating is to reduce frictional resistance with the tissues of the living body wherein the frictional resistance with the living body tissues is reduced through the lubricious surface. As a consequence, easy operations of insertion, rotation and back-and-forth movements of medical devices are ensured and such a coating is very useful in shortening the amount of procedural time and mitigating the patient's pain associated with insertion and removal.

Disposable medical devices, as a sterilized product, have been manufactured and commercially sold from pure-play companies and provided to medical institutions. Among them, most catheters are made up of synthetic polymer materials, for which ethylene oxide gas (EOG) sterilization has been adapted. In other words, for existing hydrophilic polymer-coated catheters or guide wires, EOG sterilization has been predominantly adopted in view of the concerns of material degradation and functional lowering as a product.

In recent years, there have been demanded sterilization methods using no EOG, which is a specified chemical substance (toxic substance), in consideration of environmental problems. Hence, radiation sterilizations using radiations such as a γ-ray, X-ray, electron beam (EB) and the like have been reviewed. The initial process of damaging activity (bactericidal activity or bacteriostatic activity) against microorganisms is ascribed to the reaction between an activated molecular species having high chemical reactivity, such as an ion, radical or the like, which is generated through interaction between a radiation and a constituent molecule of an organism or a molecule in the vicinity thereof, and DNA of the microorganism or other type of biomolecule. The activated molecular species is generated on the basis that with γ-ray and X-ray irradiations, high-speed electrons ejected from a substance by the action of the γ-ray further cause the substance to be ionized or excited in most cases. With electron beam irradiation, high-speed electrons are directly injected into a substance, meaning that the electron beam and g-ray and X-ray substantially have the same functional mechanism.

Taking it into consideration that when making use of normal temperature treatment and radiotransparency that are characteristic of radiation sterilization, a radiation can be irradiated from outside after packaging thereby enabling the treatment to the center, the high penetrating power of γ-rays has been a great merit. However, the performance of electron accelerators has been improved in the 1990's and thus, satisfactory permeability could be obtained, for which electron beam radiation to medical devices has been attempted and such electron beam (EB) sterilization has steadily increased in number from the latter part of the 1990's.

Where radiation sterilization is applied to medical devices that have been hitherto subjected to EOG sterilization, it is necessary to check the degradation and durability of materials and products after the radiation sterilization of intended medical devices. More particularly, it is of necessity to check mechanical characteristic changes, an unusual odor and coloration formed, and the presence or absence of elution of decomposed products after irradiation. The details thereof, especially with respect to a method of confirming merchantability in radiation sterilization, are set forth in International Standard ISO 11137.

The inventors of the present invention have engaged in application and investigation of radiation sterilization of medical devices and experienced a variety of problems involved in the investigation of electron beam sterilization applied to products that have been hitherto sterilized with EOG. Especially, as to hydrophilic polymer-coated medical devices in more detail with respect to the elution resistance and sliding performance of hydrophilic polymer-coated catheter/guide wire, we have experienced some instances where an increase in amount of an eluted matter and functional degradation (a lowering of sliding performance or lowering of lubricity) under specified conditions are more likely to occur in electron beam sterilization when comparing with EOG sterilization.

It is known that the membranes used in blood treating devices (a kidney dialysis device, a dialyzer) suffer a damage by radiation irradiation and degrade thereby increasing an amount of an eluted matter from a hollow fiber membrane. Many attempts have been proposed up to now for material degradation at the time of radiation sterilization, particularly with respect to the problem on the increased amount of an eluted matter. For instance, in Patent Document 1 and Patent Document 2, there is disclosed a sterilization method wherein when dialyzer products in a dried condition are sterilized, a deoxidant is incorporated along with a humidity controlling agent, if desired, so as to carry out sterilization substantially under oxygen-free conditions. In Patent Document 3, there is disclosed a sterilization method wherein sterilization is performed substantially under oxygen-free conditions after hermetic sealing in a gas impermeable material container along with a moisture-releasing deoxidant.

These sterilization methods are performed substantially under oxygen-free conditions and thus, cannot make use of oxygen molecular species, especially, oxygen radicals or ozone, which have strong damaging activity against microorganisms. This invites an increase in sterilization dose so as to enhance a bactericidal effect, with the attendant problem that material degradation is caused owing to the high dose. Moreover, there is concern that in the absence of oxygen, there arises a problem of proliferation of anaerobic bacteria, especially obligate anaerobes.

In order to suppress material degradation, there is disclosed, for example, in Patent Document 4, a method wherein a sterilization-protecting agent (glycerine, polyethylene glycol or the like) is contained in a hollow fiber membrane and a γ-ray is irradiated under conditions of a moisture content of not greater than 30%. However, the use of the sterilization-protecting agent is inconvenient in that sterilization-protecting agents that have never been employed for existing EOG sterilization are required, leading to cost rises. In addition, it is not favorable from the standpoint of safety and development of lubricity that sterilization-protecting agents such as glycerine, etc., are coated and left on hydrophilically-coated catheters or guide wires.

In Patent Document 5, there is disclosed an irradiation sterilization method of a blood treating device, which is characterized in that a hollow fiber membrane made of a polysulfone resin and a hydrophilic resin is sterilized by irradiation under conditions of a moisture content of not higher than 5% and a relative humidity of not higher than 40% in the atmosphere around the hollow fiber membrane.

On the other hand, as described in Patent Document 6, there is known a method of preventing a hollow fiber membrane from degrading wherein when a γ-ray sterilization is carried out, the hollow fiber membrane becomes wetted to a level not lower than a water saturation content.

By the way, when comparing Patent Document 5 and Patent Document 6 with each other, a difference in moisture content is recognized. It is considered that in the instance of Patent Document 5, this is achieved for the first time by combination of a polysulfone membrane and a hydrophilic resin. Accordingly, a difficulty is involved in applying, as it is, to hydrophilic polymer-coated catheters and guide wires making use of a variety of materials. The method of subjecting a hollow fiber membrane disclosed in Patent Document 5 to wetted conditions of not lower than a water saturation content or the sterilization method of a water-filled dialyzer are not favorable from the standpoint of transport cost rises based on the increase in weight of product and proliferation of microorganisms during transport and storage, and have never been put into practice.

Besides, in Patent Document 7, there is disclosed a high-performance hollow fiber membrane-type blood purifying device, which is characterized in that a radical spin content in the hollow fiber membrane after radiation sterilization is at not greater than $20.0 \times 10^{16}$ spins/g. In this case, the material is limited to a polysulfone film. Limitation is also placed on the case where a polysulfone-based, hollow fiber-type blood treating device is hermetically sealed, along with a deoxidant, in a container made of a gas impermeable material, under which sterilization is carried out by irradiation of a gamma ray. A difficulty is involved in applying, as it is, such a conventional technology for the radiation sterilization method of a dialyzer achieved by limiting the type of material to catheters or guide wires to which EOG sterilization has been applied up to now.

In Patent Document 8, there is disclosed, as a method of preparing a hydrophilic polymer-coated catheter, a sterilization method wherein radiation irradiation is performed during the course of wetting with a polyvinylpyrrolidone (PVP) solution. In this method, it is meant to coat the uppermost surface with crosslinked PVP. Thus, this method cannot be applied to other types of hydrophilic polymer products because polymer coating agent-derived lubricity inherently belonging to the product is changed. To use, as it is, the PVP solution containing an organic solvent upon final sterilization has concerns about safety of the residual organic solvent on a living body.

In Patent Document 9, there are disclosed, as an application of a medical hydrogel made up of different types of polymer compounds, a method wherein a solution containing a polymer of high biocompatibility and a radiation crosslinking polymer compound is coated onto a body of a medical device and subjected to radiation irradiation to fix on the surface of the medical device body, and also a method of making the medical device. In this literature, a hydrophilic polymer-coated guide wire is exemplified as a medical device and it is indicated that film formation by radiation crosslinking is possible. However, no mention is made of the lubricating performance of the guide wire, and no mention or suggestion is made of whether or not radiation sterilization is applicable to guide wires.

More particularly, the radiation sterilization technique that has been hitherto studied mainly to cope with the problem of an eluted matter from the polysulfone film of a dialyzer cannot be applied, as it is, to catheters or guide wires having been subjected to hydrophilic polymer coating. In addition, there has never been reported any technique or knowledge relating to an eluted matter and the stabilization of sliding performance in case where radiation sterilization is applied to catheters or guide wires coated with a hydrophilic polymer.

PRIOR ART DOCUMENTS

Patent Documents

Patent Document 1: Japanese Patent Laid-open No. 2006-110164

Patent Document 2: Japanese Patent Laid-open No. 2005-95270

Patent Document 3: Japanese Patent Laid-open No. 2005-95271

Patent Document 4: Japanese Patent Laid-open No. Hei 6-285162

Patent Document 5: Japanese Patent Laid-open No. 2000-288085

Patent Document 6: Japanese Patent Publication No. Sho 55-23620

Patent Document 7: Japanese Patent Laid-open No. 2005-334319

Patent Document 8: JP-T-2002-530158 Patent Document 9: Japanese Patent Laid-open No. 2004-215709

SUMMARY OF INVENTION

Technical Problem

The invention has for its object the application of radiation sterilization to medical devices having subjected to hydrophilic polymer coating.

In detail, the invention has as its object the provision of a radiation sterilization method wherein discrepancies, i.e. an increased amount of an eluted matter and/or a lowering of product performance (sliding performance), occurring during radiation sterilization of disposable medical devices coated with a hydrophilic polymer, e.g. catheters, guide wires and the like, are suppressed.

Furthermore, another object is to provide a method for manufacturing a disposable medical device wherein an increased amount of an eluted matter and/or a lowering of product performance (sliding performance) is suppressed.

Technical Solution

The present inventors have made intensive studies and, as a result, found that when radiation sterilization is performed under a controlled moisture content of a medical device, there can be achieved a radiation-sterilized medical device wherein an eluted matter is reduced in amount and sliding performance is maintained.

More particularly, the invention provides the following [1] to [14].

[1] A radiation sterilization method of medical devices, which including packaging a disposable medical device having a hydrophilic polymer coating with a gas-permeable packaging material, controlling a product moisture content, and subjecting to radiation sterilization.

[2] The radiation sterilization method as recited in [1], wherein the disposable medical device is a catheter or a guide wire.

[3] The radiation sterilization method as recited in [1] or [2], wherein the product moisture content is so controlled that the disposable medical device packaged with the gas-permeable packaging material is maintained in a predetermined humidity atmosphere for not shorter than a time at which the moisture content reaches an equilibrium.

[4] The radiation sterilization method as recited in [1] or [2], wherein the product moisture content is so controlled that the disposable medical device packaged with the gas-permeable packaging material is maintained in a humidity environment of a relative humidity of 60 to 98% RH for three hours or over.

[5] The radiation sterilization method as recited in any one of [1] to [4], wherein the gas-permeable packaging material is a moisture permeable pouch having a moisture permeability of not less than 1000 g/m²–24 hours (25° C., 90% RH) and incapable of transmitting water at a normal pressure.

[6] The radiation sterilization method as recited in any one of [1] to [5], wherein the hydrophilic polymer is made of a monoalkyl ester of methyl vinyl ether/maleic anhydride copolymer or a copolymer made primarily of said monoalkyl ester of the copolymer and a product moisture content at the time of the radiation irradiation ranges 0.1 to 0.5 mass %.

[7] The radiation sterilization method as recited in any one of [1] to [5], wherein the hydrophilic polymer is made of polyvinylpyrrolidone or a copolymer made primarily of polyvinylpyrrolidone and a product moisture content thereof at the time of radiation irradiation ranges 0.1 to 0.5 mass %.

[8] The radiation sterilization method as recited in any one of [1] to [7], wherein the radiation sterilization is effected by use of an electron beam.

[9] The radiation sterilization method as recited in any one of [1] to [7], wherein the radiation sterilization is effected by use of a γ-ray.

[10] The radiation sterilization method as recited in any one of [1] to [7], wherein the radiation sterilization is effected by use of an X-ray.

[11] A method for manufacturing a medical device, which including providing a disposable medical device having a hydrophilic polymer coating, packaging said medical device with a gas-permeable packaging material, controlling a product moisture content, and subjecting to radiation sterilization.

[12] The manufacturing method as recited in [11], wherein the product moisture content is controlled by maintaining the disposable medical device packaged with the gas-permeable packaging material in a predetermined humidity atmosphere for not shorter than a time at which the moisture content reaches an equilibrium.

[13] The manufacturing method as recited in [11] or [12], wherein the product moisture content is controlled by maintaining the disposable medical device packaged with the gas-permeable packaging material in a humidity environment of a relative humidity of 60 to 98% RH for three hours or over.

[14] The manufacturing method as recited in [11] to [13], wherein the gas-permeable packaging material is a moisture permeable pouch having a moisture permeability of not less than 1000 g/m²–24 hours (25° C., 90% RH) and incapable of transmitting water at a normal pressure.

Advantageous Effect

According to the radiation sterilization method of the invention, medical devices that have been hitherto subjected to EOG sterilization can be radiation-sterilized as it is without adding any change thereto. Especially, with respect to hydrophilic polymer-coated catheters and/or guide wires, sterilized products which strike a balance between an elution resistance and a lubrication performance can be provided. Moreover, because of no use of EOG having concern about toxicity, medical devices of high quality can be stably provided to medical fronts while reducing an environmental load. In addition, no use of chemicals enables a simple procedure and leads to high safety.

MODE FOR CARRYING OUT THE INVENTION

Figure 1:
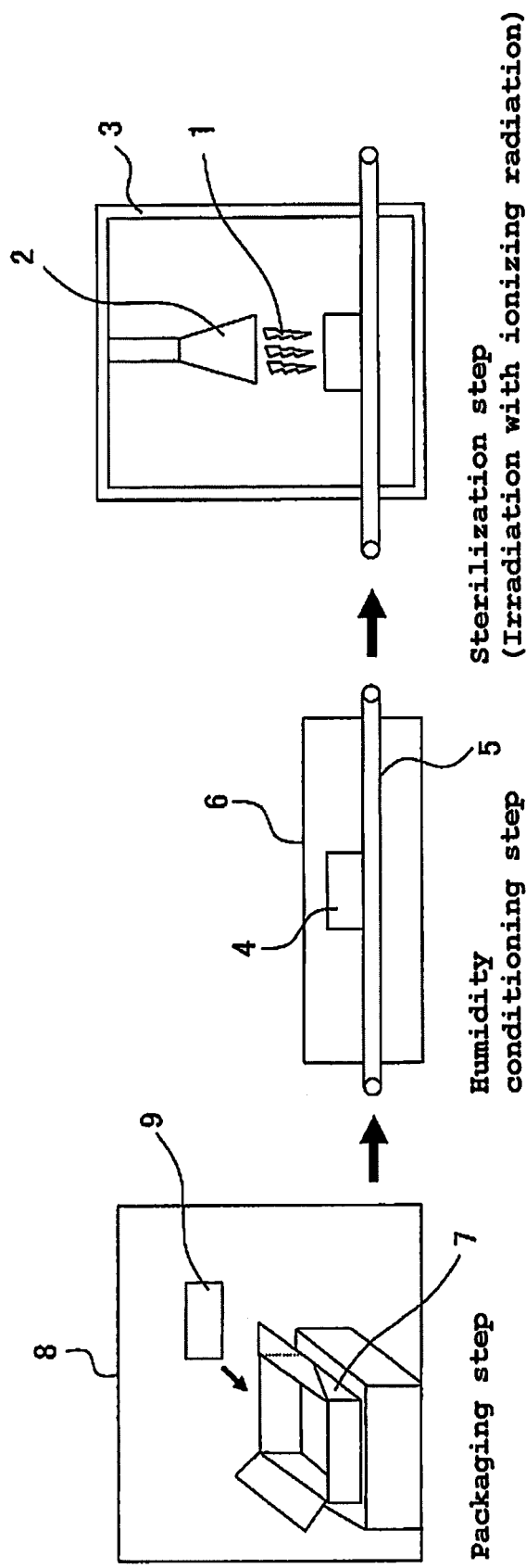
FIG. 1 is a schematic view of an example of a radiation sterilization method of the invention.

In the invention, although radiation sterilization is carried out under control of a product moisture content, an embodiment represented in the schematic view (FIG. 1) showing an overall flow is preferred. More particularly, an embodiment is particularly preferred, which includes "packaging step" of packaging with a gas-permeable packaging material, "sterilization step" of irradiating a medical device with an ionizing radiation, and "humidity conditioning step" of controlling a product moisture content after the "packaging step" but before the "sterilization step."

Although there may be used an embodiment wherein the "humidity conditioning step" of controlling a product moisture content is provided between the "making step" of making (providing) a medical device and the "packaging step" of packaging with a gas-permeable packaging material, the first-mentioned embodiment wherein the "humidity conditioning step" of controlling a product moisture content is provided after the "packaging step" of packaging with a gas-permeable packaging material is preferred. The sterilization originally means the act of stochastically reducing microorganisms in number and does not mean a completely aseptic condition. In this sense, there is some possibility of proliferating microorganisms in case of a product that is kept wetted, for which limitation is not placed only on such an embodiment. If a product is packaged at an early stage, the handling performance in subsequent steps is drastically improved.

In the "packaging step," medical devices after completion of processing and assembling of starting materials are individually placed in protective members (trays or tubes), which are designed to be readily, appropriately taken out into a packaging material capable of keeping a sterilized condition. In the "packaging step," an individually packaged medical device, for example, in the form shown in FIG. 2 may be collected in the form of a shipping box, or may be delivered to a next step in the form of the individual package. The delivery in this stage intends to mean one making use of a conveyor although not limited thereto, and the delivery means may be any means such as a unmanned carrier, a manned forklift or the like.

As a packaging material used for the individual package, there are selected gas-permeable packaging materials with an excellent radiation resistance. Although usable packaging materials should be adapted for "Package of Finally Sterilized Medical Devices" of International Standard (ISO 11607), such materials may be appropriately selected from commercially available sterilization packaging materials for medical use. For packaging materials and packaging forms, there may be usable, for example, center seal gazette pouches made of plastic films inserted with a waterproofing tape, paper or specialized paper/plastic film stickers, paper or specialized paper/paper or specialized paper stickers, or paper or specialized paper/plastic sheet blister packages. Since the "humidity conditioning step" is carried out prior to the radiation sterilization step, it is preferred to use individual packages made up of a gas permeable material.

The packaging material should preferably be a permeable packaging pouch having a moisture permeability of not lower than 1000 g/m$^2$-24 hours (25° C., 90% RH) and having gas permeability not permitting water to be passed at a normal pressure. This is considered due to the fact that humidity conditioning becomes difficult when the moisture permeability is not greater than 1000 g/m$^2$-24 hours (25° C., 90% RH) and that if the material is so permeable as to allow water passage, a resistance to permeability of the spores of bacteria lowers although these limitations are not placed only for these reasons.

Figure 2:
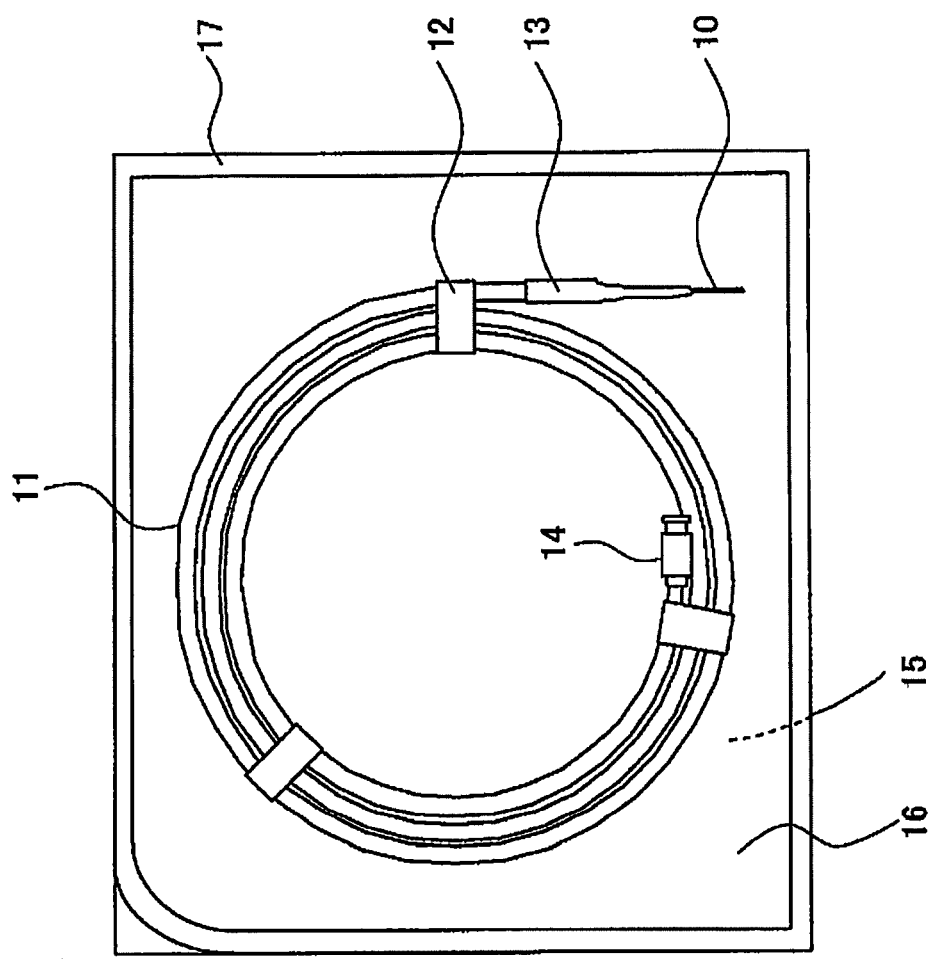
FIG. 2 is a view showing an example of a package for a medical device, which is subjected to a radiation sterilization method of the invention.

In more detail, the packaging material is preferably a sticker of specialized paper/plastic film in combination. For instance, as shown in FIG. 2, there is preferably used a packaging material including a gas-permeable specialized paper 15 provided at a mounting side and a transparent film 16 at an upper side. In a more preferred embodiment, Tyvek (registered trade name of Du Pont) is used as part of a gas permeable material of the specialized paper. This is mainly due to the consideration of reliability and past results although not always limited thereto. Water vapor permeable resin films, composite products of the resin films and woven or non-woven fabrics or medical latex-impregnated coated papers may be used as the part. It will be noted that the specialized paper used herein means ones wherein resin fibers are thermopressed into a paper-like sheet or a resin-coated paper, with a good radiation resistance.

An instance of a preferred packaging material and packaging form is as exemplified in FIG. 2. A hydrophilically coated guide wire body (10) is accommodated in a polyethylene resin holder tube (11) for protection, and the holder tube is circularly fixed with holder clips (12). The guide wire body (10) is protected with an inserter part (13) at a tip side thereof. A holder hub (14) is attached to a distal end side of the inserter (13) of the holder tube (11). The materials of 11, 12, 13 and 14 in FIG. 2 may be any thermoplastic resins, respectively, and are not limited to specific types of materials. A specialized paper (15) such as Tyvek is made into a pouch by heat sealing a polyethylene side of a multi-layered plastic transparent film (16) such as of polyester/polyethylene with a seal portion (17).

The "packaging step" of the medical device is air-conditioned to provide predetermined temperature and humidity, ventilation frequency and cleanliness factor in order to keep an manufacturing environment within GMP standard values defined in the Pharmaceutical Affairs Law. For instance, the temperature is controlled within 19 to 23° C., the relative humidity is within 25 to 50% RH, and the cleanliness factor is within Class 100 to 10,000. According to Chronological Scientific Tables, the annual average humidity of from 1971 to 2000 in Tokyo is at 63% RH. It may be said that the manufacturing environment of medical devices is controlled at relatively low humidity thereover.

In the "humidity conditioning step," the medical device packaged with a gas-permeable packaging material and intended for sterilization is placed in a given humidity environment so that the moisture present in the product is equilibrated thereby providing a constant product moisture content. Although the control is enabled by the product moisture content, it is more preferred to control by use of a humidity conditioning time. This is due to the consideration of simplicity although not limited thereto.

Where a hydrophilic polymer-coated product (a hydrophilic polymer-coated guide wire) packaged with a gas-permeable packaging material is allowed to stand in a constant humidity environment, the time required for saturation of the product moisture content is about three hours when the product moisture content in every given time is measured by use of a trace moisture meter for polymer (Aquatrac Plus, made by C.W. Brabender Instruments, Inc.). With medical device products coated with other types of hydrophilic polymers, it takes about three hours as well. In most cases, the product moisture content in one hour is on the way of moisture absorption and is thus apt to vary.

The medical device made in a constant humidity environment is held at an equilibrated moisture content in that environment. In order to attain a desired product moisture content, it is efficient to control the content in terms of a time at which a moisture content reaches an equilibrium in a given humidity environment without resorting to a sampling procedure of a product for measurement of the product moisture content. The product moisture content may vary depending on the type of intended medical device. More particularly, it will be readily understood that if the types of materials used differ, the product moisture content differs depending on the intended medical device.

Where compatibility between the reduction of an eluted matter and the maintenance of sliding performance of medical devices is discussed, the product moisture content alone is insufficient to cover medical devices constituted of a wide variety of materials. However, control with a product moisture content is possible if a product is specified as one made of specified constituents. Here, importance is placed on humidity conditioning conditions where a product moisture content becomes equilibrated. This can be controlled in terms of the time of keeping in a predetermined humidity atmosphere. The measurement of the product moisture content is possible by use of any of measuring techniques known to those skilled in the art making use of the trace moisture meter mentioned before, an increase in weight and the like.

The relative humidity in the "humidity conditioning step" is preferably at not less than 60% RH, more preferably at 60 to 98% RH and much more preferably at 70 to 98% RH. The humidity in the "making step" is generally controlled, for example, at a relative humidity of 25 to 50% RH. The moisture content of a product is more influenced with an environmental humidity than with time. This is because a higher environmental humidity leads to a higher equilibrated moisture content of a product although not limited only to these reasons. In this connection, however, a relative humidity of 100% RH or over is unfavorable. This is because there may be some cases where dew condensation occurs on a product to leave traces of waterdrops on a packaging material and cause the packaging material to be wrinkled after drying, thereby resulting in a poor appearance. Additionally, an excessively water-absorbed state such as created by immersion in water is also unfavorable because of the possibility that the sliding performance of a product lowers.

With the case of 25° C. (room temperature) in the "humidity conditioning step," a medical device is in a given humidity environment preferably for one hour or over, more preferably for three hours or over.

The product moisture content can be controlled, as stated before, by control of a retention time in a given humidity environment. If products can be specified as having a similar structure, a similar size or similar constituent materials, direct control with a moisture content of product is possible. In this connection, for example, in the case of a guide wire making use of a Ni—Ti wire coated with a contrast agent-incorporated polyurethane, equilibrated moisture contents of plastic-type guide wires coated with a variety type of hydrophilic polymers are, for example, approximately at 0.4 mass % when allowed to stand at 98% RH. When allowed to stand in an ordinary room environment at a humidity of approximately 50% RH, the moisture content is at about 0.1 mass %. Accordingly, the product moisture content prior to irradiation can be controlled within a range of 0.1 to 0.5 mass %. The product moisture content is preferably controlled within 0.1 to 0.5 mass %. This is because at 0.1 mass % or below, an increase in amount of an eluted matter over non-sterilized products is found and in a state of a moisture excess as much as 1.0 mass % or over, a lowering of sliding performance occurs although not limited thereto. In this regard, however, since the moisture content of an intended medical device differs depending on the type of material constituent, such a preferred range of moisture content as mentioned above is directed to the case of the hydrophilically coated plastic-type guide wire.

The inventors of, the present invention have found that as to hydrophilic polymer-coated products, when they are subjected to radiation irradiation in a dried state, the hydrophilic polymer undergoes decomposition reaction, an eluted matter increases in amount and that when radiation irradiation is carried out in an excessively water-absorbed condition, the hydrophilic polymer undergoes crosslinking reaction, thereby causing a lowering of sliding performance. More particularly, in the invention, attention has been focused on the fact that the likelihood of decomposition reaction and crosslinking reaction of a hydrophilic polymer upon radiation irradiation of a hydrophilic polymer-coated product depends on the moisture content in the hydrophilic polymer layer. This leads to suppressing the increase in amount of an eluted matter and sliding performance from degrading by control of the product moisture content.

For simplicity in the course of operations in actual product sites, the invention also enables the product moisture content to be controlled by a retention time in a given humidity atmosphere.

In the "humidity conditioning step," the retention may feasible inside a constant humidity chamber in a batchwise manner, or a delivery step per se may be air-conditioned by means of an air conditioner at a humidity of 60 to 98% RH, so that delivery and humidity conditioning may be performed simultaneously.

In the "sterilizing step," an irradiation chamber of a radiation may be subjected to humidity control, if desired. The humidity control in the irradiation chamber is not always essential. This is because the product moisture content is kept, without any substantial variation, within several hours after humidity conditioning owing to the moisture retentivity of a hydrophilic polymer per se.

It is preferred to further include, after the "sterilization step," "drying step" of drying the sterilized, hydrophilic polymer-coated medical device. This is intended for preventing microorganisms from proliferation during distribution and storage although not limitative to this intention. In this regard, however, where distribution and storage periods are apparently short, the "drying step" may not be included.

The hydrophilic polymer-coated product is subjected to priming with a physiological saline solution or the like immediately before use by use of an injector or the like (not shown) from the holder hub (13) and taken out from the holder tube (11). Since the device is so designed as to show lubricity only when wetted with water, whether the product is dried or not does not present any problem in practical use. In this regard, however, it is preferred from the standpoint of microorganism proliferation that a wire guide product remains dried during the course of delivery and storage. Drying after sterilization may be effected by any of techniques known in the art including, aeration with dried air, vacuum drying and the like.

No specific consideration is needed for the "sterilization step." Electron beams (EB), γ-ray, X-ray and the like are usable.

When an electron beam is used, it is preferred to use an electron accelerator having an acceleration voltage of 0.2 to 10 MeV. More preferably, a large-scaled electron accelerator having an acceleration voltage of 5 to 10 MeV is used. A higher acceleration voltage results in higher electron beam permeability, so that sterilization in the form of shipping boxes is possible although not limitative thereto.

When a γ-ray is used, use as a beam source can be made preferably of cobalt 60 ($^{60}Co$) or cesium 137 ($^{137}Cs$) and more preferably of cobalt 60 ($^{60}Co$)

Where an X-ray is used, this ray may be generated by any of methods known by the skilled in the art. It is preferred to use converted X-rays generated by subjecting an accelerated electron beam to collision with a target of a heavy metal (e.g. molybdenum, tungsten, tantalum or the like). In this case, the acceleration voltage is preferably at 5 MeV or below.

The sterilization dose used is generally at 15 to 60 kGy, for example. The sterilization dose is determined according to the method described in "Guideline Related to the Sterilization Validation of Medical Devices" (PMSB/CND Notification No. 69 by the Director of Compliance and Narcotics Division, Pharmaceutical and Medical Safety Bureau, Ministry of Health and Welfare, dated May 1, 1998). Although depending on the number of resident micobiota and the shipping form, the sterilization dose accorded thereto is adopted in the practice of the invention. More particularly, if the sterilization dose according to the Guideline or the demand of an export country is at 25 kGy, such a sterilization dose is used. The sterilization dose used herein means a minimum dose during sterilization. In actual products, a dose distribution is established, so that the performance of a commercial product to be confirmed leads to a dose at not lower than a maximum level of the dose distribution. For instance, where the sterilization dose is at 25 kGy and a dose distribution ratio within the product is set at maximum dose/minimum dose=2, it is necessary to confirm the product performance at a level of not smaller than 25×2=50 kGy. A margin of the dose variation is increased by 10%, for which testing at 55 kGy is carried out in most cases. The dose distribution within the product varies, for same commercial products, depending on the shipping form. Accordingly, consideration should be paid to the influences, on the performance of medical devices, of the sterilization dose accorded to the sterilization validation guideline and the maximum permissible dose ascribed to the dose distribution.

The hydrophilic polymer-coated medical devices, to which the sterilization of the invention is directed, include, for example, catheters for intravascular diagnosis and curing such as angiographic catheters, guide wires, vasodilation catheters (balloons), sheath introducers, microcatheters, thermodilution catheters, penetration catheters for coronary artery and the like, and effluent/reflux catheters such as urethral catheters and drainage tubes. More particularly, mention is made of medical devices that are hydrophilically coated so as to reduce a frictional resistance to a living body.

Figure 3:
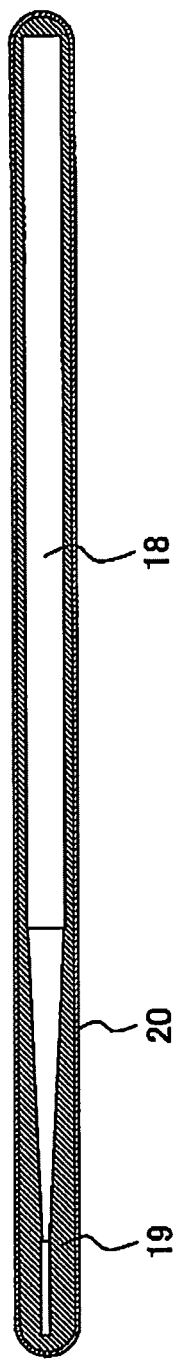
FIG. 3 is a sectional view of a hydrophilic polymer-coated guide wire, which is subjected to a radiation sterilization method of the invention.

A guide wire (FIG. 3) is exemplified as a typical medical device having subjected to hydrophilic polymer coating, for which the sterilization of the invention is intended. Constituent materials of a hydrophilically coated guide wire are now described in detail. FIG. 3 shows an example of a hydrophilically coated guide wire called plastic type. A contrast agent-containing resin coating layer (19) is formed on a metallic core wire (18) which is tapered as becoming gradually finer toward a tip side. As a material of the core wire (18), it is usual to mainly use stainless steels, nickel-titanium alloys, β-titanium alloys, or cobalt alloys. In the practice of the invention, no limitation is placed on the type of material of the core wire. The diameter ranges 0.2 to 2.0 mm and the length of the core wire (18) generally ranges 0.1 to 5.0 m, among which a most widely employed length is at approximately 1.5 m. The resin coating layer (19) may be either present or absent, and it is usual to provide a resin coating. There is known some case wherein a metal coil coverage is used in place of a resin (not shown). The coated resin is formulated with a contrast agent in a thermoplastic resin wherein an X-ray impermeable material such as tungsten, barium sulfate or the like is kneaded as a contrast agent. As the resin for the resin coating layer (19), polyurethanes have been, in most cases, adopted because of the flexibility and fixation of a hydrophilic polymer.

In the practice of the invention, it is essential that the outermost surface in contact with a living body be made of a hydrophilic polymer, and no limitation is placed on the type of material for guide wire, the diameter or the length of guide wire. Desired guide wires may be used so far as they are made of such materials and have such structures, diameters and lengths as ordinarily employed. In this regard, however, when a core wire made of a metal material and having such a great diameter that a γ-ray and an electron beam is impermeable is used, there may be some case where how to irradiate should be taken into account.

A hydrophilic polymer (20) is coated directly on the metal material of the core wire (18) or on the resin coating layer (19). Although this coating may be in the form of a single layer or a multilayer and may be or may not be subjected to covalent bonding, it should preferably have an excellent peel resistance. The principle that a hydrophilic polymer-coated medical device shows lubricity is based on the formation of a lubricating layer ascribed to the retention of a large amount of moisture in the hydrophilic polymer coating (20). The development of the surface lubricity occurs after water absorption of the hydrophilic polymer from an aqueous solvent such as a physiological saline solution, buffer solution, blood or the like. More particularly, it is considered that the lubricity occurs in such a way that water existing in the material surface develops a lubricating function owing to the fluid lubrication at an interface in contact with a blood vessel wall.

In the present specification, the hydrophilic polymer means polymer compounds whose water absorption rate is not less than 1% when immersed in a physiological saline solution. The hydrophilic polymers, to which the invention is applicable, preferably include coating compositions derived from those polymers of hydrophilic organic monomers, oligomers, prepolymers or copolymers including vinyl alcohol, N-vinylpyrrolidone, N-vinyllactam, acrylamide, amides, styrenesulfonic acid, a combination of vinyl butyral and N-vinylpyrrolidone, 2-ethyl-2-oxazoline, hydroxyethyl methacrylate, acrylic acid, vinyl methyl ether, vinylpyridinium halides, melamine, maleic anhydride/methyl vinyl ether, vinylpyridine, ethylene oxide, ethylene oxide ethylene imine, glycol, vinyl acetate, vinyl acetate/crotonic acid, methyl cellulose, ethyl cellulose, carboxymethyl cellulose, pullulan, hyaluronic acid, α-polyglutamic acid (α-PGP), ε-polylysine (ε-PLL), hydroxyethyl cellulose, hydroxypropyl cellulose, hydroxymethyl ethylcellulose, hydroxypropyl methylcellulose, cellulose acetate, cellulose nitrate, starch, gelatin, albumin, casein, gum, alginate, hydroxyethyl (meth) acrylate, hydroxypropyl(meth)acrylate, ethylene glycol (meth) acrylate, N-alkyl (meth) acrylamide, N,N-dialkyl (meth) acrylamide, N-hydroxyalkyl (meth) acrylamide polymer, N,N-dihydroxyalkyl (meth)acrylamide polymer, ether polyol, polyethylene oxide, polypropylene oxide, poly(vinyl ether), alkyl vinylsulfone, alkyl vinylsulfone acrylate, or combinations thereof. The fixation method on a medical device surface may be appropriately selected from those methods preferred for every starting material.

Industrially available, preferred hydrophilic polymers include monoalkyl esters of methyl vinyl ether/maleic anhydride copolymer (GANTREZ (registered trade name) series, by ISP (International Specialty Products) Inc.), and polyvinylpyrrolidone (PVP) and copolymers thereof (PVP, PVP/VA series, by ISP Inc.). These are favorably usable as an inexpensive convenient hydrophilic coating polymer. For instance, the copolymer mainly composed of a monoalkyl ester of methyl vinyl ether/maleic anhydride copolymer means one wherein the main component is present at not less than 80 mass %. The copolymer containing polyvinylpyrrolidone as a main component means one wherein the main component is present at not less than 80 mass %.

Preferred embodiments of the invention have been illustrated hereinabove although the invention should not be construed as limited thereto.

EXAMPLES

A series of test results using same materials are summarized in Table 1 as Examples 1 to 7 and Comparative Examples 1 to 10. With reference to Table 1, Examples 1 to 7 and Comparative Examples 1 to 10 are now described.

The invention is particularly illustrated based on the examples and comparative examples although the invention should not be construed as limited to the examples and may be carried out in any way so far as the essential constitutions defined in the claims are included.

Examples 1 to 7

Product to be Sterilized

In Example 1, there were used plastic type guide wires (commercial products) having an outer diameter of 0.038 inches (about 0.97 mm) and a length of 150 cm. This guide wires were individually packaged with a gas-permeable packaging material partly making use of Tyvek (Du Pont) in the form of a package exemplified in FIG. 2. The structure of the guide wire is one exemplified in FIG. 3, in which a Ni—Ti alloy was used as a wire and the coating resin used was a tungsten (contrast agent) incorporated polyurethane resin, respectively. As a result of analysis, the hydrophilic polymer of this guide wire was analytically found to contain a monoalkyl ester of methyl vinyl ether/maleic anhydride copolymer.

<Humidity Conditioning Step>

In the form of the package, the guide wire product was vacuum dried, followed by maintaining in a constant temperature and humidity chamber at a temperature of 40° C. and at a relative humidity of 75% RH for 24 hours (Examples 1 to 4). After the conditioning, the moisture content of the respective guide wires was measured by use of a trace moisture meter for polymer (Aquatrac Plus, made by C.W. Brabender Instruments, Inc.). The product moisture contents of Examples 1 to 4 after 24 hours were at 0.18 mass % on average. In Examples 5 to 7, conditioning was performed in a humidity environment of 25° C.-98% RH for one, three and six hours, respectively. After the conditioning, the product moisture contents of Examples 5 to 7 were, respectively, at 0.174 mass %, 0.231 mass % and 0.295 mass %.

<Radiation Sterilization Step>

Subsequently to the humidity conditioning step, electron beam sterilization was carried out by use of a 10 MeV accelerator (Rhodotron Model TT-200), made by Rhodotron. In Examples 1 to 4, sterilization doses were, respectively, set at 15 kGy, 30 kGy, 45 kGy and 60 kGy. In Examples 5 to 7, sterilization doses were set at 55 kGy. This is because assuming that a dose distribution of an actual product (wherein a shipping form is taken into consideration) in case of a sterilization dose of 25 kGy is at 2, the margin of a dose variation is taken by 10% and a maximum permissible dose is set at 55 kGy. The sterilization dose used herein means a cumulative addition dose, which is measured by use of a FWT dosimeter attached to the product and indicates an absorption dose (which may also be called "irradiation dose") actually irradiated on the product. In Examples 1 to 7, in order to perform accurate dose irradiation, simple electron beam irradiation, which rarely generates a dose distribution, was carried out.

<Eluted Matter>

As an eluted matter test, measurement of an evaporation residue was effected in accordance with the Approval Standard VII-4 for Dialysis-type Artificial Kidney Apparatus. More particularly, one guide wire product was placed in 100 ml of purified water and extracted under conditions of 50° C.-24 hours. 20 ml of the resulting extract was taken and evaporated to dryness, followed by comparing the weights [mg] of evaporation residues. In the Approval Standard VII-4 for Dialysis-type Artificial Kidney Apparatus, an adaptation criterion required is such that the evaporation residue was at 1.0 mg or below. As to the slidability of guide wire, a guide wire was immersed in a physiological saline solution after removal from the pouch and the degrees of sliding were compared with one another by a hand's touch.

It will be noted that in Examples 1 to 7, vacuum drying was effected prior to the humidity conditioning step, and this was carried out for the purposes of aligning initial conditions of the humidity conditioning step with those of the comparative examples. Accordingly, upon application to actual products, the vacuum drying prior to the humidity conditioning is not always essential.

Comparative Examples 1 to 10

In Comparative Examples 1 to 10, guide wire products of the same manufacture lot as those guide wires employed in Examples 1 to 7 were used. The differences between Examples 1 to 7 and Comparative Examples 1 to 10 are such that at least one of the humidity conditioning step and the radiation sterilization step was not carried out in Comparative Examples 1 to 10. In Comparative Examples 2 to 5, 8 and 9, the humidity conditioning step was not carried out but the radiation sterilization step alone was performed. In Comparative Example 6, although the humidity conditioning step (40° C.-75% RH-24 hours) was carried out, no radiation sterilization step was effected. In Comparative Examples 1, 7 and 10, neither humidity conditioning step nor radiation sterilization step was carried out. With Comparative Example 7, no electron beam sterilization was carried out and an EOG-sterilized product was used as it is for comparative reference. In this case, a product stored in a product warehouse was used, so that no vacuum drying was effected. Comparative examples 1, 6, 7 and 10 making use of products stored in a product warehouse were those instances of an irradiation of 0 kGy, which were for comparison and reference in the respective series in order to elucidate the influences of electron beam irradiation. It will be noted that these were non-sterilized ones and could not be used in actual clinical service. In Comparative Example 8, electron beam irradiation at 55 kGy was carried out without carrying out vacuum drying and humidity conditioning. Comparative Example 9 was studied as supersaturation condition of moisture content in order to confirm the influences of moisture content. In Comparative Example 9, water priming treatment was performed in place of humidity conditioning, followed by electron beam irradiation (55 kGy). The priming treatment means that a guide wire product is wetted with a physiological saline solution or water while placing in a holder tube (11). A physiological saline solution or purified water was injected into the holder tube (11) by means of an injector, and excess water was blown away by air injection again from the injector. In this case, the moisture content of a product was approximately at 1.0 mass % and thus was in the range of 0.5 to 2.0 mass % (measured value: 1.740 mass %). This method (priming) could not allow products to be uniformly absorbed with water and the products were apt to vary in moisture content.

The results of evaluation of Examples 1 to 7 and Comparative Examples 1 to 10 are shown in Table 1.

TABLE 1

| Examples | Irradiation dose [kGy] | Elution amount [mg] | Product moisture content [%] | Sliding resistance Evaluation by hand's touch | Sliding resistance value [gf] (sliding cycles) 1 | 25 | 50 | Humidity conditioning step or pretreatment for sterilization |
|---|---|---|---|---|---|---|---|---|
| Example 1 | 15 | 0.38 | 0.176 | ○ | — | — | — | Standing under 40° C.-75% RH-24 hrs. |
| Example 2 | 30 | 0.56 | 0.176 | ○ | — | — | — | Standing under 40° C.-75% RH-24 hrs. |
| Example 3 | 45 | 0.58 | 0.176 | ○ | — | — | — | Standing under 40° C.-75% RH-24 hrs. |
| Example 4 | 60 | 0.67 | 0.176 | ○ | 34 | 35 | 36 | Standing under 40° C.-75% RH-24 hrs. |
| Example 5 | 55 | 0.78 | 0.174 | ○ | 35 | 33 | 32 | 25° C.-98% RH-1 hr. |
| Example 6 | 55 | 0.67 | 0.231 | ○ | 35 | 33 | 33 | 25° C.-98% RH-3 hrs. |
| Example 7 | 55 | 0.61 | 0.295 | ○ | 35 | 35 | 35 | 25° C.-98% RH-6 hrs. |
| Comparative Example 1 | 0 | 0.35 | 0.057 | ○ | — | — | — | Vacuum dried for 3 days |
| Comparative Example 2 | 15 | 0.42 | 0.057 | ○ | — | — | — | Vacuum dried for 3 days |
| Comparative Example 3 | 30 | 0.63 | 0.057 | ○ | — | — | — | Vacuum dried for 3 days |
| Comparative Example 4 | 45 | 0.66 | 0.057 | ○ | — | — | — | Vacuum dried for 3 days |
| Comparative Example 5 | 60 | 0.88 | 0.057 | ○ | — | — | — | Vacuum dried for 3 days |
| Comparative Example 6 | 0 | 0.36 | 0.176 | ○ | — | — | — | Unsterilized: standing under 40° C.-75% RH-24 hrs. |
| Comparative Example 7 | 0 | 0.46 | 0.080 | ○ | 33 | 33 | 34 | No humidity conditioning, product stored in warehouse, EOG sterilization |
| Comparative Example 8 | 55 | 0.91 | 0.069 | ○ | 35 | 33 | 32 | No humidity conditioning, product stored in warehouse |
| Comparative Example 9 | 55 | 0.42 | 1.740 | x | 38 | 83 | 165 | Water priming |
| Comparative Example 10 | 0 | 0.53 | 0.078 | ○ | 37 | 35 | 33 | No humidity conditioning, product stored in warehouse, unsterilization |

— unexamined

Note:
Hydrophilically coated guide wires used as samples were all from the same manufacturing lot having an outer diameter of 0.038 inches and a length of 1.5 m.

A graph (FIG. 5) is prepared based on the measured values of Table 1. The graph (FIG. 5) shows the relation between the irradiation dose and the elution amount. In both examples and comparative examples, the elution amount increased with an increasing irradiation dose. This indicates that the decomposition reaction of the hydrophilic polymer by application of the electron beam is correlated with an increase of irradiation dose. It will be seen that this decomposition reaction is more suppressed in the examples than in the comparative examples. Identification of the eluted matter by instrumental analysis revealed that the matter was a decomposed matter of the hydrophilic polymer. The decomposition reaction means partial elimination of the hydrophilic polymer through conversion to a low molecular weight matter, and the hydrophilic polymer coating per se is sufficiently left on the product. This is considered why there is no difference in sliding performance between Examples 1 to 4 and Comparative Examples 1 to 6. Although there is no difference in sliding performance between the electron beam sterilization and the unsterilization, an eluted matter increases in amount, with the attendant problem on the collateral of chemical, physical and biological safeties. Accordingly, it has been judged from the standpoint of the safety that the electron beam sterilization of the hydrophilic polymer should be such that the irradiation dose is drastically lowered, or moisture should be given to the hydrophilic polymer so as to suppress the decomposition reaction.

Figure 4:
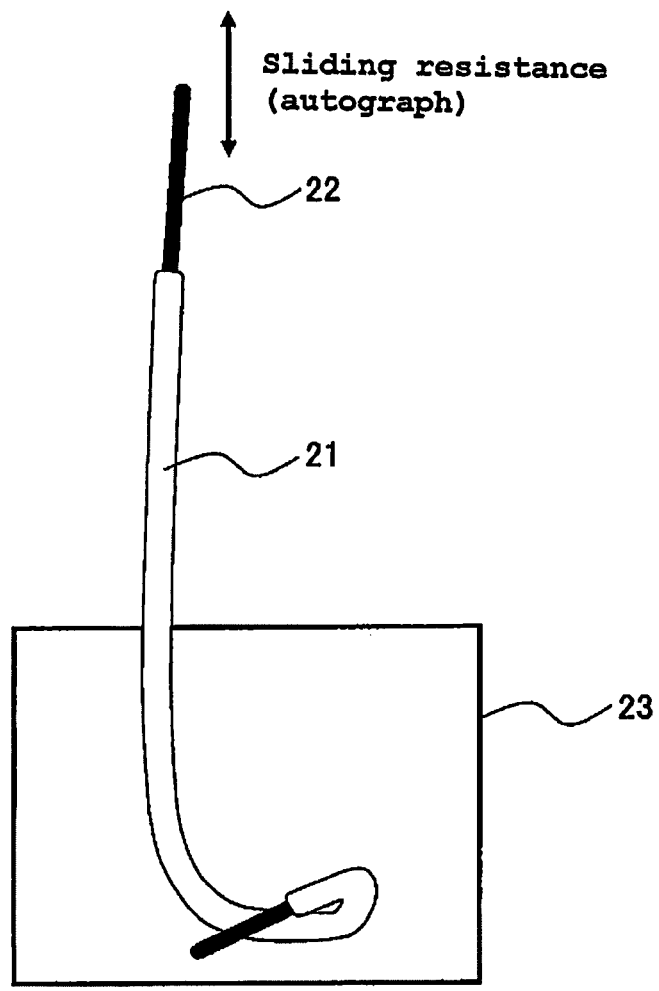
FIG. 4 is a schematic view of a method of evaluating slidability of a guide wire.

The sliding performances of Comparative Examples 7, 8 and 9 and Example 4 were relatively evaluated with one another using an evaluation system shown in FIG. 4. Based on the results, a graph (FIG. 6) was prepared. This graph (FIG. 6) shows the relation between the sliding cycle and the resistance value (i.e. durability of lubrication performance), and FIG. 7 shows elution amounts of Comparative Examples 7, 8 and 9 and Example 4 compared with one another.

The evaluation system shown in FIG. 4 is one that enables the sliding resistance values to be numerically, relatively compared with one another by use of an instrument (tensile tester: autograph) relating to the frictional resistance of a catheter and a guide wire on actual clinical use. Using the autograph, an operation of forcing a guide wire into and withdrawing from a 5Fr-sized big catheter is repeated. The sliding resistance value is a value obtained by recording, in every sliding cycle, a forced resistance value [gf] of the guide wire. The value of 20 to 50 [gf] in Comparative Example 7 (EOG sterilized product) is one that enables the catheter to be clinically operated without problem (in view of clinical results). When this value is at not less than 60 [gf], a doctor has a feeling of strangeness or feels heavy during operation of the catheter. Additionally, when the value is at not less than 100 [gf], a doctor will judge the feeling of strangeness at such a level that catheter handling should be stopped. At not less than 200 [gf], when forced into, the guide wire undergoes a deflection with resistance, thus being judged at such a level that the back-and-forth movement, of the guide wire becomes impossible and the wire is clinically non-usable. These values have been empirically known by the present inventors having engaging in long-term manufacture and distribution of guide wires.

Figure 5:
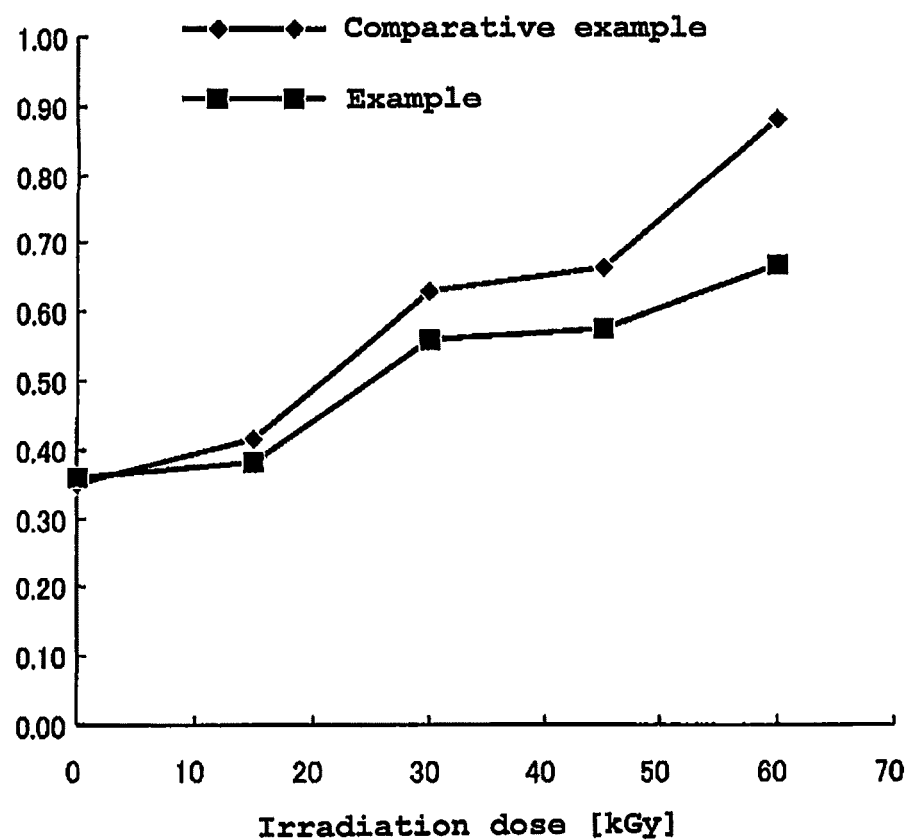
FIG. 5 is a graph showing the relation (dose dependency) between an elution amount and an irradiation dose.

In Example 4 and Comparative Examples 7 and 8, it was found that the sliding performances by hand's touch after the sterilization were same and that the sliding resistance values determined by the evaluation system of FIG. 5 were at a level free of clinical problem. Comparative Example 7 is directed to an existing EOG sterilized product and Comparative Example 8 is directed to an electron beam-sterilized product (55 kGy). FIG. 7 reveals that the elution amount of an eluted matter from the electron beam-sterilized product of Comparative Example 8 is larger, thus leaving a problem on safety collateral. The results are those of a 1.5 m long product. If the length is at not smaller than 1.5 m, there is the high possibility of exceeding the standard of 1.0 [mg] and thus, limitation has to be placed on the length.

Figure 6:
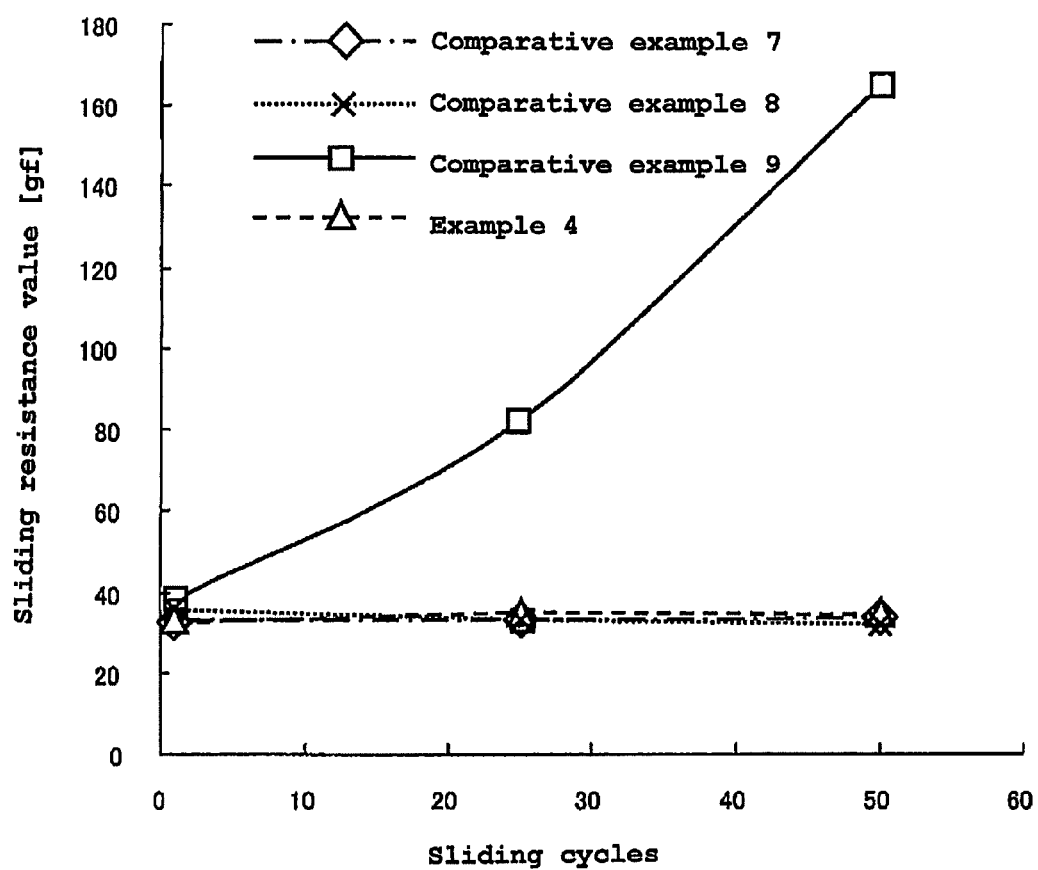
FIG. 6 is a graph comparing changes of sliding resistance value in every sliding cycle.
Figure 7:
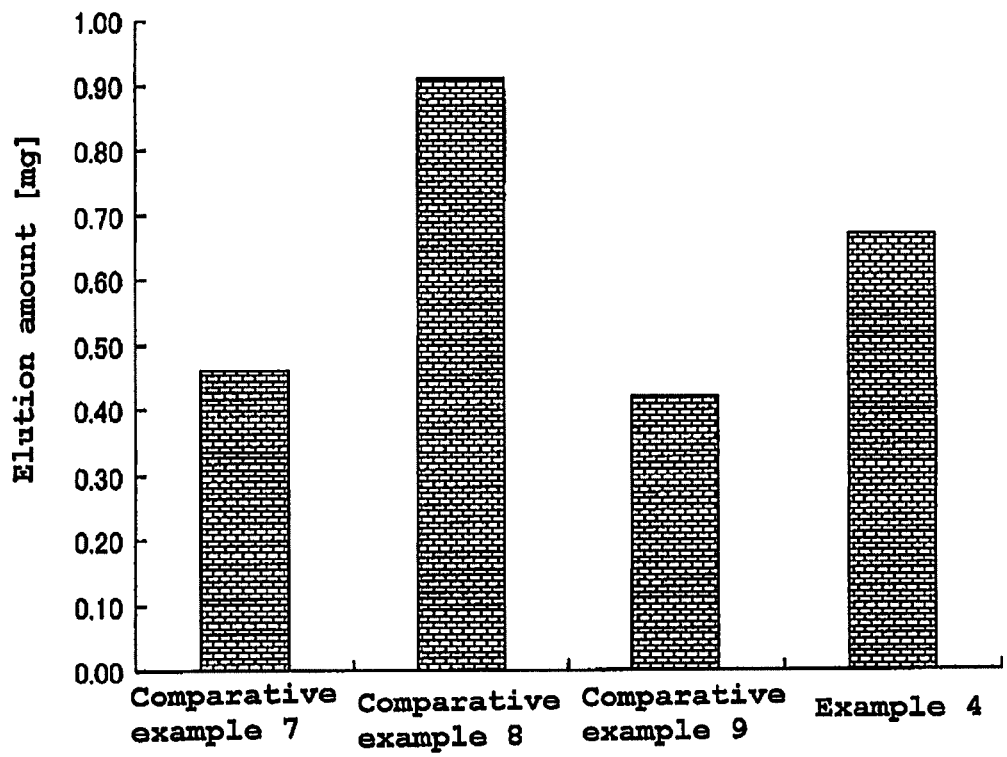
FIG. 7 is a graph comparing elution amounts.

From FIG. 6, it will be seen that with an electron beam-sterilized wire contained with excess water as in Comparative Example 9, the sliding resistance value becomes worse as the cycles become larger in number. More particularly, there is no stability of sliding performance. In other words, the durability of lubricity of the hydrophilic polymer becomes degraded. From FIG. 7, the cause of lowering the reduction of an eluted matter in Comparative Example 9 and the durability of slidability in FIG. 6 is considered to result from the radiation crosslinkage (crosslinking reaction) occurring at the hydrophilic polymer coating layer (20) in the presence of excess water. The hydrophilic polymer coating layer (20) becomes hard and brittle as a film through the crosslinkage and is liable to peel off, for which the durability of the sliding performance is considered to lower.

In Example 4, the slidability is not lowered and an elution amount of an eluted matter is relatively small and thus, such a wire is within a scope of approval standards and can be judged as a permissible product.

Figure 8:
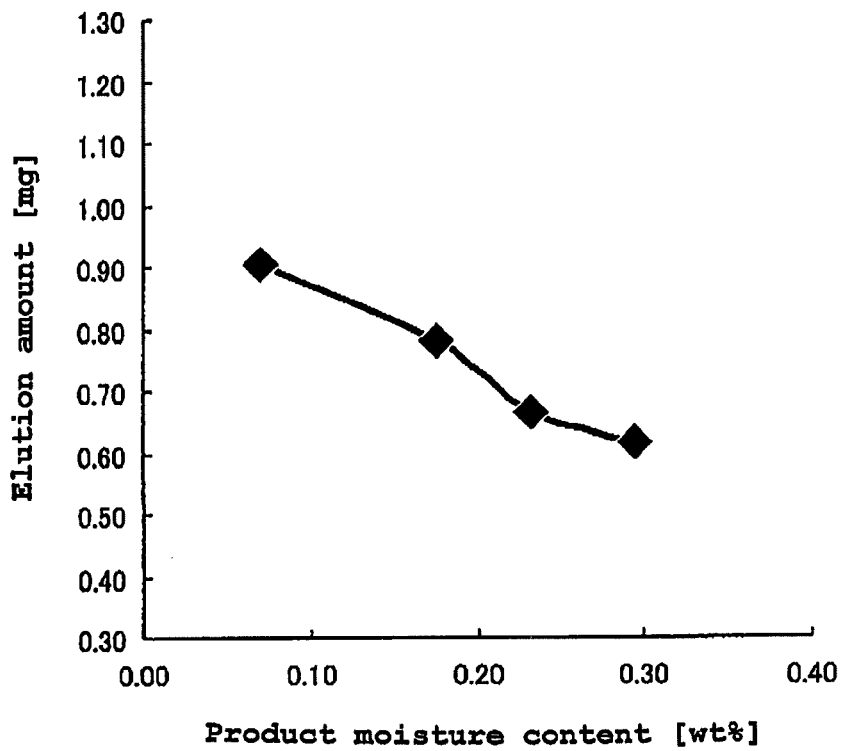
FIG. 8 is a graph showing the relation between an elution amount and a product moisture content.
Figure 9:
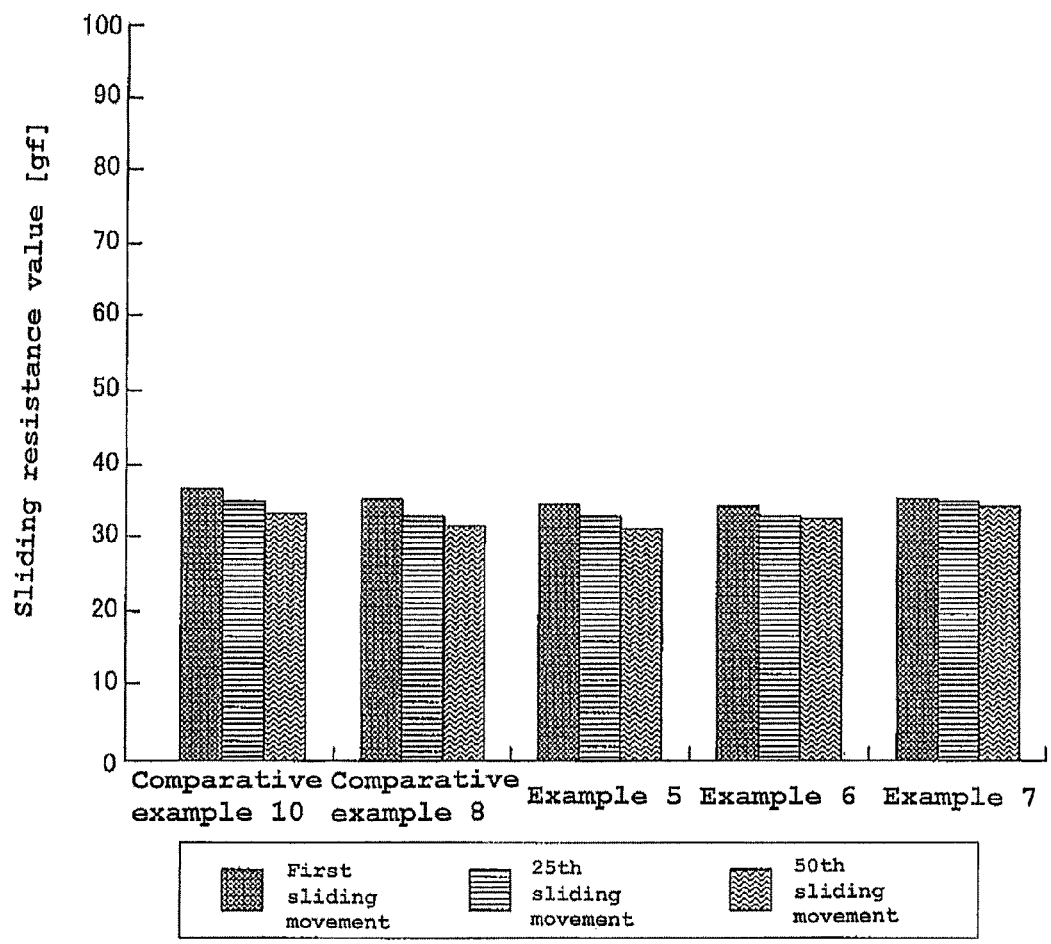
FIG. 9 is a graph comparing sliding performances.

From Examples 5 to 7 and Comparative Example 8, there is obtained a relation between the product moisture content and the elution amount (irradiation dose: 55 kGy) as depicted in a graph (FIG. 8) and thus, the correlation between the product moisture content and the elution amount has been recognized. In a product moisture content ranging 0.1 to 0.4 mass %, a first-order correlation coefficient $R^2$ is at 0.98 and is thus close to 1. Accordingly, it is indicated that the elution amount can be controlled with the product moisture content. At this time, the product moisture content is controlled with the retention time in a constant humidity environment. In place of the control with the product moisture content, the control with the retention time in a constant humidity environment may be possible. At the time, the sliding resistance value in the graph (FIG. 9) is at 50 [gf] or below, thus maintaining a good sliding performance. The saturated moisture content of product under ordinary storage conditions is approximately at 0.1 mass % when the product is allowed to stand in an environment of a relative humidity of 50% RH. Thus, when radiation sterilization is effected by controlling a product moisture content within 0.1 to 0.5 mass % or by allowing to stand in a constant humidity environment for one hour or over, preferably for three hours or over thereby absorbing moisture to saturation, the eluted matter can be suppressed within a reference value range and a good sliding performance is ensured.

Example 8 and Comparative Examples 11 to 14

Although the invention has been illustrated in detail in regard of Examples 1 to 7 and Comparative Examples 1 to 10, the invention is applicable to hydrophilic polymer coated catheters other than hydrophilically coated guide wires. For instance, indwelling bladder balloon catheters making use of a thermoplastic elastomer are illustrated using Example 8 and Comparative Examples 11 to 13.

Figure 10:
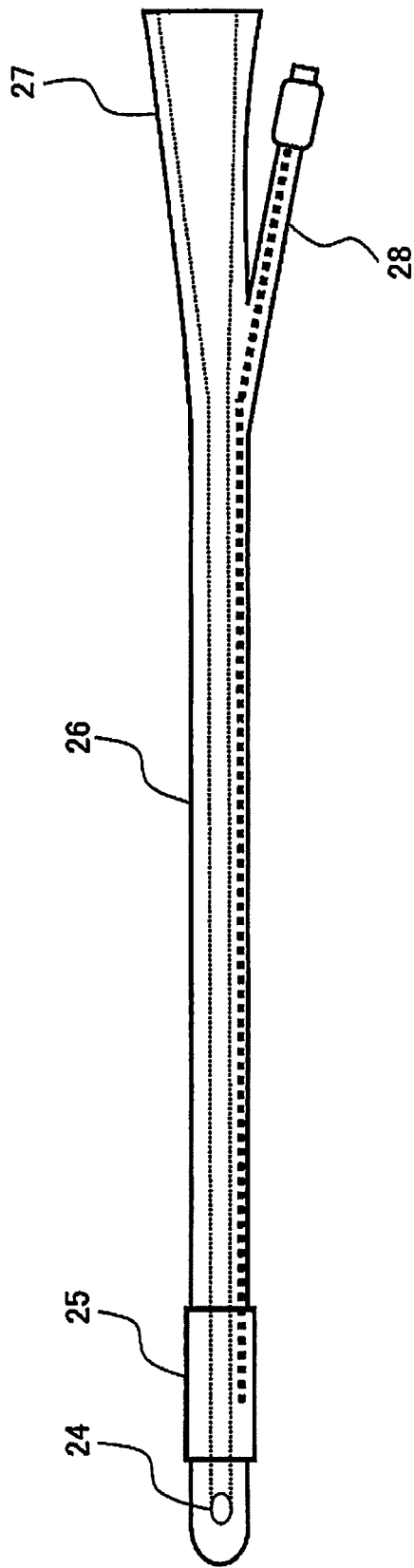
FIG. 10 is a graph showing an external appearance of an example of a hydrophilic polymer-coated indwelling bladder balloon catheter subjecting to a radiation sterilization method of the invention.

In Example 8 and Comparative Examples 11 to 13, there were used hydrophilically coated, commercially available indwelling bladder catheters. An outline view of the indwelling bladder catheter is shown in FIG. 10. The catheter is made of an SEBS resin and has a polyvinylpyrrolidone (PVP) coating at an outermost surface as a hydrophilic coating. In use, the catheter is wetted with a physiological saline solution, water or the like and is inserted into the urethral meatus from a catheter tip side. After the insertion, a balloon (25) is inflated with air or the like from an inflation port (28), thereby permitting it to be indwelled in the bladder. Urine in the bladder is discharged from an effluent port (27) associated with an effluent hole (24) into a urine-introducing bag or the like. Because such a relatively large catheter as of 18 Fr is inserted into the urethral tube, the coating makes insertion and removal operations easy, thereby resulting in the unlikelihood of damaging the urethral tube.

Figure 11:
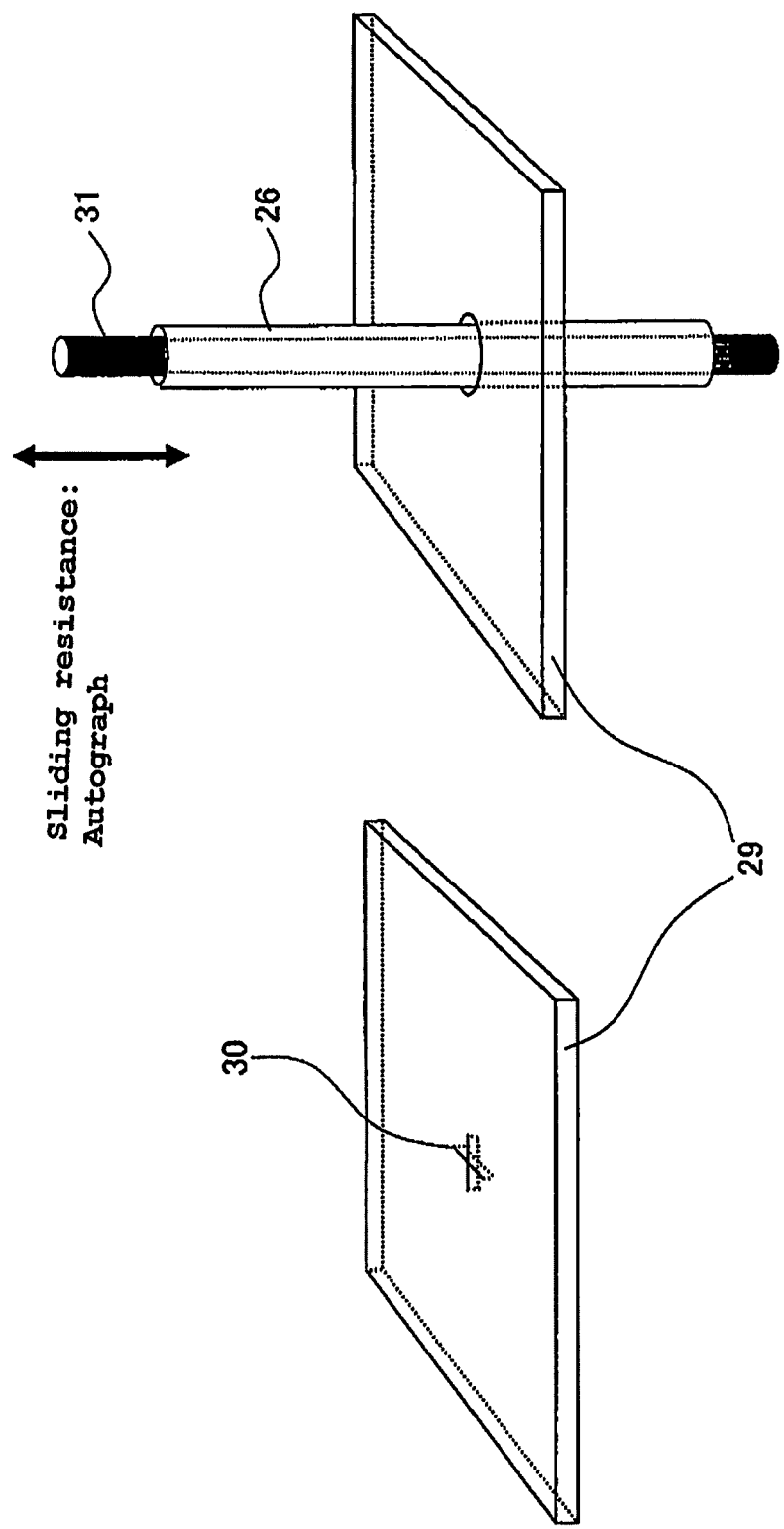
FIG. 11 is a schematic view of a method of evaluating slidability of an indwelling bladder balloon catheter.

A catheter shaft (26) of FIG. 10 was cut into an about 10 cm long straight, hydrophilically coated piece that is just proximal from the balloon (25), and a stainless steel cored bar (31) having a size substantially close to the inner diameter of a waste lumen was passed therethrough as shown in FIG. 11. This was slidably moved at a stroke of 3 cm and a reciprocation speed of 500 mm/minute in such a state as to pass through a 1 mm thick silicone sheet (29) having a cross slit (30) therein, thereby obtaining a sliding resistance value. At this time, the sliding resistance was measured by use of the autograph provided that a forcing stress was indicated in terms of [gf] unit. During the course of the sliding movement, water was continuously poured over the catheter so as not to allow drying. The relative evaluation was made by use of this evaluation system. As to the correlation between this evaluation system and a clinical system, it was empirically found that a sliding resistance value of not larger than 50 gf was within a practical range and if this value was within 20 gf, patients suffered substantially no pain upon catheter insertion and removal.

A catheter size of 18 Fr., was provided. An unsterilized catheter was provided for Comparative Example 11, one obtained by subjecting to EOG sterilization as a sterilization method was for Comparative Example 12, one obtained by subjecting an unsterilized product to electron beam sterilization (55 kGy) without performing humidity conditioning was for Comparative Example 13, and one obtained by subjecting an unsterilized product to water priming and electron beam sterilization (55 kGy) was for Comparative Example 14. Moreover, a catheter obtained by subjecting an unsterilized product to humidity conditioning (25° C.-90% RH-six hours) and electron beam sterilization (55 kGy) was provided for Example 8. The product moisture content prior to humidity conditioning was at 0.023 mass % and a product moisture content after the humidity conditioning (25° C.-90% RH-six hours) was at 0.036 mass %.

Figure 12:
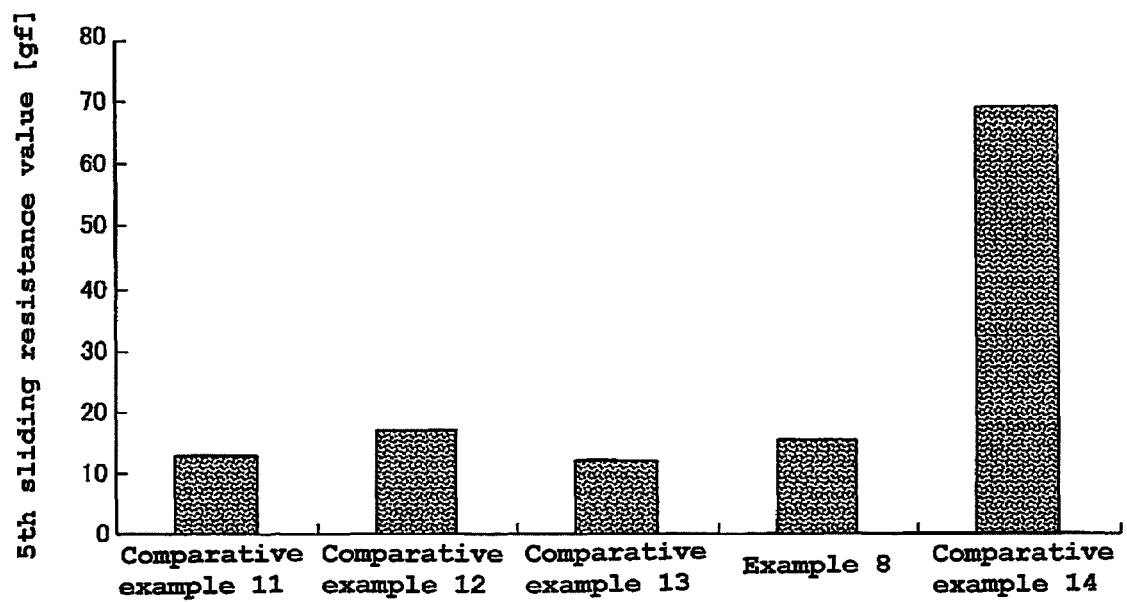
FIG. 12 is a graph comparing slidabilities of indwelling bladder balloon catheters for different sterilization methods.

FIG. 12 shows, for comparison, sliding resistance values [gf] (values at the fifth sliding cycle) for different sterilization methods. Even when using PVP as a hydrophilic coating polymer and a resin material and a catheter structure differing from those of the guide wire, a similar tendency as with the case of the hydrophilically coated guide wires of Examples 1 to 7 was obtained. More particularly, Comparative Examples 11 to 13 and Example 8 were similar to one another with respect to the sliding performance and maintained the sliding performance when using electron beam irradiation after humidity conditioning. In Comparative Example 14 wherein water priming was effected just before the irradiation, the sliding performance worsened extremely. As to the eluted matter, no difference between comparative examples 11 to 14 and Example 8 was recognized on the basis of the indwelling bladder catheter standards. This is considered for the reason that the amount of the lubrication coating was very small relative to the whole body of catheter. As shown in the example, the radiation sterilization after humidity conditioning according to the invention enables radiation sterilization to be applicable to the hydrophilic polymer-coated catheter, to which application of only EOG sterilization has been hitherto considered possible.

DESCRIPTION OF REFERENCE NUMERALS

1: Electron beam
2: Irradiation hone
3: Shielding wall
4: Product
5: Conveyor
6: Humidity conditioning space
7: Shipping box
8: Clean room
9: Individual package: product
10: Guide wire body
11: Holder tube
12: Holder clip
13: Inserter
14: Holder hub
15: Gas-permeable specialized paper (mount side)
16: Transparent film (upper face side)
17: Heat-sealed portion (sealed portion)
18: Core wire
19: Coated resin layer
20: Hydrophilic polymer coating
21: PT catheter
22: GW
23: Water vessel
24: Waste liquid hole
25: Balloon portion (shrunk state)
26: Shaft portion
27: Waste liquid port
28: Balloon inflation port
29: Silicone sheet
30: Cross slit
31: Cored bar

The invention claimed is:

1. A radiation sterilization method of medical devices, comprising packaging a disposable medical device having a hydrophilic polymer coating in a gas-permeable packaging material so that the entirety of the disposable medical device is positioned in the gas-permeable packaging material, controlling a product moisture content, and subjecting the disposable medical device packaged in the gas-permeable packaging material to radiation sterilization, wherein said product moisture content is controlled by maintaining said disposable medical device packaged within the gas-permeable packaging material in an environment having a relative humidity of 60% to 98% RH for three hours or over.

2. The radiation sterilization method as defined in claim 1, wherein said disposable medical device is a catheter or a guide wire.

3. The radiation sterilization method as recited in claim 1, wherein the gas-permeable packaging material is a moisture permeable pouch having a moisture permeability of 1000 g/m$^2$-24 hours or over when measured at a temperature of 25° C. and a relative humidity of 90% and incapable of transmitting water at a normal pressure.

4. The radiation sterilization method as defined in claim 1, wherein the hydrophilic polymer is made of a monoalkyl ester of methyl vinyl ether/maleic anhydride copolymer or a copolymer made primarily of the monoalkyl ester of the copolymer and a moisture content of the medical device at the time of the radiation irradiation ranges 0.1 to 0.5 mass %.

5. The radiation sterilization method as defined in claim 1, wherein the hydrophilic polymer is made of polyvinylpyrrolidone or a copolymer made primarily of polyvinylpyrrolidone and a moisture content of the medical device at the time of radiation irradiation ranges 0.1 to 0.5 mass %.

6. The radiation sterilization method as recited in claim 2, wherein the gas-permeable packaging material is a moisture permeable pouch having a moisture permeability of 1000 g/m$^2$-24 hours or over when measured at a temperature of 25° C. and a relative humidity of 90% and incapable of transmitting water at a normal pressure.

7. The radiation sterilization method as defined in claim 2, wherein the hydrophilic polymer is made of a monoalkyl ester of methyl vinyl ether/maleic anhydride copolymer or a copolymer made primarily of the monoalkyl ester of the copolymer and a moisture content of the medical device at the time of the radiation irradiation ranges 0.1 to 0.5 mass %.

8. The radiation sterilization method as defined in claim 2, wherein the hydrophilic polymer is made of polyvinylpyrrolidone or a copolymer made primarily of polyvinylpyrrolidone and a moisture content of the medical device at the time of radiation irradiation ranges 0.1 to 0.5 mass %.

9. A method for manufacturing a medical device, comprising providing a disposable medical device having a hydrophilic polymer coating, packaging said medical device in a gas-permeable packaging material so that the entirety of the disposable medical device is positioned in the gas-permeable packaging material, controlling a product moisture content, and subjecting the disposable medical device packaged in the gas-permeable packaging material to radiation sterilization, wherein said product moisture content is controlled by maintaining said disposable medical device packaged within the gas-permeable packaging material in an environment having a relative humidity of 60% to 98% RH for three hours or over.

10. The manufacturing method as defined in claim 9, wherein said gas-permeable packaging material is a moisture permeable pouch having a moisture permeability of 1000 g/m$^2$-24 hours or over when measured at a temperature of 25° C. and a relative humidity of 90% and incapable of transmitting water at a normal pressure.

11. A method of radiation sterilizing medical devices, comprising;
- packaging a disposable medical device inside gas-permeable packaging material to produce a packaged disposable medical device, the disposable medical device packaged inside the gas-permeable packaging material including a hydrophilic polymer coating;
- controlling moisture content of the packaged disposable medical device;
- subjecting the packaged disposable medical device to radiation sterilization to sterilize the disposable medical device packaged inside the gas-permeable packaging material; and
- drying the disposable medical device packaged inside the gas-permeable packaging material, the drying occurring after the radiation sterilization,
- wherein said moisture content is controlled by maintaining said disposable medical device packaged within the gas-permeable packaging material in an environment having a relative humidity of 60% to 98% RH for three hours or over.

12. The manufacturing method as defined in claim 11, wherein said gas-permeable packaging material is a moisture permeable pouch having a moisture permeability of 1000 g/m$^2$-24 hours or over when measured at a temperature of 25° C. and a relative humidity of 90% and incapable of transmitting water at a normal pressure.

* * * * *